United States Patent [19]
Rampal

[11] Patent Number: 6,013,789
[45] Date of Patent: Jan. 11, 2000

[54] COVALENT ATTACHMENT OF BIOMOLECULES TO DERIVATIZED POLYPROPYLENE SUPPORTS

[75] Inventor: Jang B. Rampal, Yorba Linda, Calif.

[73] Assignee: Beckman Coulter, Inc., Fullerton, Calif.

[21] Appl. No.: 09/026,742

[22] Filed: Feb. 20, 1998

[51] Int. Cl.$^7$ .................................................. C07H 21/00
[52] U.S. Cl. .............................. 536/25.3; 435/6; 422/50; 422/68.1
[58] Field of Search ................. 536/25.3; 435/6; 935/77.78; 422/50, 68.1

[56] References Cited

U.S. PATENT DOCUMENTS 5,474,895  12/1995  Ishii et al. ..................................... 435/6
5,514,785   5/1996  Van Ness et al. ...................... 536/22.1
5,683,875  11/1997  Lichtenwalter ............................. 435/6

OTHER PUBLICATIONS

Lund, V., et al., "Assessment of methods for covalent binding of nucleic acids to magnetic beads, Dynabeads™, and the characteristics of the bound nucleic acids in hybridization reactions", *Neucleic Acids Res.*, 16(22):10861 (1988).

Matson, R. S., et al., "Biopolymer Synthesis on Polypropylene Supports: Oligonucleotide Arrays", *Anal. Biochem.* 224:110 (1995).

Rasmussen, S.R., et al., "Covalent Immobilization of DNA onto Polystyrene Microwells The Molecules Are Only Bound at the 5' End, "*Anal. Biochem.* 198:138 (1991).

Schott, H., *Affinity Chromatography*, Chapters 3 and 4 (pp. 15–44), Marcel Dekker, Inc. (1984).

Southern, E. M., et al., "Analyzing and Comparing Nucleic Acid Sequences by Hybridization to Arrays of Oligonucleotides: Evaluation Using Experimental Models", *Genonmics* 13:1008 (1992).

Weiler, J., et al., "Combining the Preparation of Oligonucleotide Arrays and Synthesis of High–Quality Primers", *Anal. Biochem.*, 243:218 (1996).

*Primary Examiner*—Ardin H. Marschel
*Attorney, Agent, or Firm*—William H. May; Margaret A. Kivinski

[57] ABSTRACT

Disclosed herein is a method for attaching pre-synthesized oligonucleotides to a polypropylene support medium. Most preferably, a polypropylene film is aminated by a plasma discharge in the presence of ammonia gas. An oligonucleotide having a terminal phosphate is activated in the presence of an imidazole and a carbodiimide to form a phosphorimidazolide. The activated oligonucleotide becomes immobilized by forming a phosphoramidate bond with the aminated polypropylene. The invention can be used to construct oligonucleotide arrays for hybridization assays.

24 Claims, 8 Drawing Sheets

= Polypropylene

EDC = 1-ethyl-3-(3-dimethylaminopropyl)-carbodiimide

Im = N-Methylimidazole or 4,5-Dicyanoimidazole

= Polypropylene

EDC = 1-ethyl-3-(3-dimethylaminopropyl)-carbodiimide

Im = N-Methylimidazole or 4,5-Dicyanoimidazole

Lane: 1    2
Lane 1 hybridized with oligo A-918
and lane 2 with 63 bp wild type PCR Probe: 3'Phosphate oligo 4,5-DCI

COVALENT ATTACHMENT OF BIOMOLECULES TO DERIVATIZED POLYPROPYLENE SUPPORTS

TECHNICAL FIELD OF THE INVENTION

The present invention is directed to the covalent attachment of pre-synthesized oligonucleotides and other biomolecules onto surface activated organic polymers. The method is particularly useful for the construction of oligonucleotide arrays, which can be used for reverse blot hybridizations, sequencing by hybridization, and genetic testing.

BACKGROUND OF THE INVENTION

Nucleic acid hybridization is a fundamental technique in molecular biology. Nucleic acid hybridization assays have been used extensively in molecular biology to establish the sequence similarity of populations of nucleic acids. Hybridization is simply the annealing or pairing of single stranded nucleic acid molecules (DNA or RNA) to form double strands. The most common technique employing hybridization is the Southern blot hybridization technique, in which a set of unknown target DNA molecules is immobilized on a membrane and a solution containing labeled DNA probe molecules is used to bathe the membrane under conditions where complementary molecules will anneal (Southern, E. M. Detection of specific sequences among DNA fragments separated by gel electrophoresis. *J. Mol. Biol.* 98:503–517 (1975)). In an analogous technique called Northern blot hybridization (Alwine J. C. et al. Method for detection of specific RNAs in agarose gels by transfer to diazobenzyloxymethyl-paper and hybridization with DNA probes. *Proc. Natl. Acad. Sci.* 74:5350–5354 (1977); Alwine, J. C. et al. Detection of specific RNAs or specific fragments of DNA by fractionation in gels and transfer to diazobenzyloxymethyl paper. *Methods Enzymol.* 68:220–242 (1979)), RNA molecules immobilized on membranes are the targets. The labeled probe DNA used in the liquid phase can be as short as 10 to 20 nucleotides. The probes are usually labeled with radioisotopes, although other reporter groups, e.g. fluorescein, biotin, etc., can be used.

Reverse blot hybridization employs the opposite approach. Instead of immobilizing unknown DNAs, a set of well defined DNA probes are immobilized on a solid surface and the unknown labeled DNA is present in the liquid phase. Theoretically, a high density array containing a large number of probes can be used for reverse hybridizations with a single target molecule. By decoding the hybridization pattern of the unknown DNA to positions of known sequence on the solid phase array, sequence information from several positions of the unknown target DNA can be obtained. While the idea of sequencing by hybridization (SBH) has generated much excitement, the use of reverse hybridization assays to detect known DNA sequences and their alterations is a more practical application at present.

Several methods for the constructing biomolecule arrays of sufficiently high density for sequencing applications are currently under development. Arrays of peptides and oligonucleotides have been created using photolithographic techniques. (Fodor, S. P. A., et al., Light-Directed Spatially Addressable Parallel Chemical Synthesis, *Science* 251:767–773 (1991); Pease, A. C., et al., Light-generated oligonucleotide arrays for rapid DNA sequence analysis, *Proc. Natl. Acad. Sci. USA* 91:5022–5026 (1994)) Biomolecules are attached to reactive groups on the surface of a solid support, which can be selectively blocked or deblocked through the use of photolabile protecting groups. Alternatively, a physical mask may be used and the desired chemical reactions carried out on the unmasked portion of the support. (Southern, E. M. et al. Analyzing and comparing nucleic acid sequences by hybridization to arrays of oligonucleotides: Evaluation using experimental models. *Genomics* 13:1008–1017 (1992)) A third alternative is a printer-like device, which can deposit an array of drops on the matrix. (U.S. Pat. No. 5,474,796) Despite these promising early developments, existing or suggested methods do not reliably produce the very large high density arrays needed for sequencing applications in a rapid and reproducible manner.

There are two fundamental ways of immobilizing oligonucleotides at specific sites on solid supports: the oligonucleotides may be synthesized on the solid phase in their respective positions, i.e., in situ, or they may be synthesized apart from the solid support and attached later. The former method has been successfully achieved in several different ways. The first reverse hybridization arrays were made using glass modified with an aliphatic poly(ether) linker as a solid support (Southern, E. M. et al. 1992). More recently, polypropylene was used as a support for the in situ synthesis of oligonucleotides (U.S. Pat. No. 5,554,501).

There are also various methods available for immobilizing pre-synthesized biomolecules onto solid supports. Such methods include: simple adsorption, ultra violet cross linking or covalent attachment. In adsorption and ultra violet crosslinking, the attachment of molecules onto the surface of the support is by random process. Moreover, the specific sites can become inaccessible to binding with complementary sequences. In a covalently coupled system, the attachment of the functionalized or activated oligonucleotide to the surface of the polymeric support is at specific sites.

In general, the attachment of standard oligonucleotides to unmodified glass or plastic surfaces is inefficient. For this reason, many investigators trying to immobilize oligonucleotides modify them with molecules that promote adsorption or enable attachment to the support. Oligonucleotides modified with bovine serum albumin adsorb passively to microtiter plates designed to bind protein molecules (Southern, E. M. International Patent Application PCT GB 89/00460 (1988)). Biotinylated oligonucleotides bind tightly to plates or beads that are coated with avidin or streptavidin. Oligonucleotides with polythimidylate tails have been photochemically crosslinked to nylon (Bains, W., et al., A novel method for nucleic acid sequence determination. *J. Theoret. Biol.* 135:303–307 (1988)). More recently, oligonucleotides with terminal amino (Drmanac, R., et al. Sequencing of megabase plus DNA by hybridization: Theory of the method. *Genomics* 4:114–128 (1989), Lysov et al. Determination of the DNA nucleotide sequence by hybridization with oligonucleotides. A new method. *Proc USSR Acad. Sci* 303:1508–1511 (1988)) or methyluridine (Khrapko, K. R., et al., An oligonucleotide hybridization approach to DNA sequencing. *FEBS Lett.* 256:118–122 (1989)) groups have been covalently crosslinked to compatible reactive groups on multi-well plate surfaces.

Another approach is to modify the solid support with a suitable functional group and/or linker. For example, there are numerous reports of DNA becoming covalently bound to polystyrene supports, which carry different active groups on their surfaces, e.g., hydroxyl, carboxyl, amine, aldehyde, hydrazine, epoxide, bromoacetyl, maleimide and thiol groups (U.S. Pat. No. 5,474,895; Lund, V., et al., Assessment of methods for covalent binding of nucleic acids to magnetic beads, DynabeadsJ, and the characteristics of the bound nucleic acids in hybridization reactions, *Nucleic Acids Research* 16:10861–10880 (1988)) or having a spacer arm ending with an active group (Rasmussen, S. R., et al., Covalent Immobilization of DNA onto Polystyrene Microwells: The Molecules Are Only Bound at the 5' End, *Anal. Biochem.* 198:138–142 (1991)). However, these methods generally entail trade offs between high coupling yields and non-specific binding of nucleic acids during subsequent hybridization procedures.

Immobilizing pre-synthesized oligonucleotides and in situ synthesis have different advantages for array construction. Synthesis in situ does not involve the handling of thousands of independent oligonucleotides, each of which must be produced on a scale that far exceeds what is required for the array. In contrast, the ability to freely arrange the members of an array after oligonucleotide synthesis is only possible with pre-synthesized oligonucleotides.

Thus, a need exists for immobilizing procedures that permit greater flexibility in constructing arrays of pre-synthesized oligonucleotides on suitable solid supports. Preferably, the attachment procedures are amenable to automation using repeatable steps in order to facilitate their use in the clinical laboratory.

SUMMARY OF THE INVENTION

The above identified needs and the shortcomings of prior art systems are overcome by the present invention, which provides a practical procedure for attaching pre-synthesized oligonucleotides and other biomolecules onto polypropylene. The covalently attached oligonucleotides can then serve as probes for target DNA in a hybridization reaction. Moreover, the polypropylene-linked oligonucleotides are compatible with the use of fluorescence-labeled target nucleic acids or oligonucleotides during hybridization.

The polypropylene is modified with an amine, the amination being accomplished by means of the application of energy in the microwave or radio-frequency bands to the polypropylene in the presence of an amine containing gas. Preferably, the energy is applied by a radio-frequency plasma discharge, a microwave frequency plasma discharge, or a corona discharge.

In a particularly preferred embodiment of the invention, the amine is derived from an ammonia gas and the elevated energy state is achieved via radio frequency plasma discharge.

The aminated polypropylene is then utilized for attachment of a pre-synthesized oligonucleotide. The amine groups on the activated polypropylene are reactive with the oligonucleotide such that the oligonucleotide is covalently attached onto the surface of the polypropylene. The attachment reaction activates an oligonucleotide, which has a terminal phosphate, by combining the oligonucleotide with an imidazole and a carbodiimide to form a phosphorimidazolide. When the activated oligonucleotide is deposited on the aminated solid support oligonucleotide becomes covalently attached to the solid support. After a short reaction period of at least about 5 min, any unattached oligonucleotide can be washed from the solid support.

The polypropylene can be in the form of films, membranes, filaments, beads, microtiter plates, foams, frits, and threads. For some purposes, such as the creation of oligonucleotide arrays, the polypropylene is most preferably in the form of a biaxially oriented film.

The oligonucleotides attached to polypropylene supports are particularly useful in the areas of reverse dot blots, sequencing by hybridization, and genetic analysis for the purposes of medical and diagnostic evaluation. Because polypropylene is chemically inert, problems associated with non-specific binding are substantially avoided so that detection sensitivity is significantly improved. Moreover, since polypropylene has a relatively low background fluorescence, it is well suited for fluorescence detection procedures.

In particularly preferred embodiments, pre-synthesized oligonucleotides complementary to regions of genes of interest are attached to the polypropylene support, and these in turn are used for the analysis of patient samples for the presence or absence of particular genetic mutation(s).

DETAILED DESCRIPTION OF THE INVENTION

Figure 1:
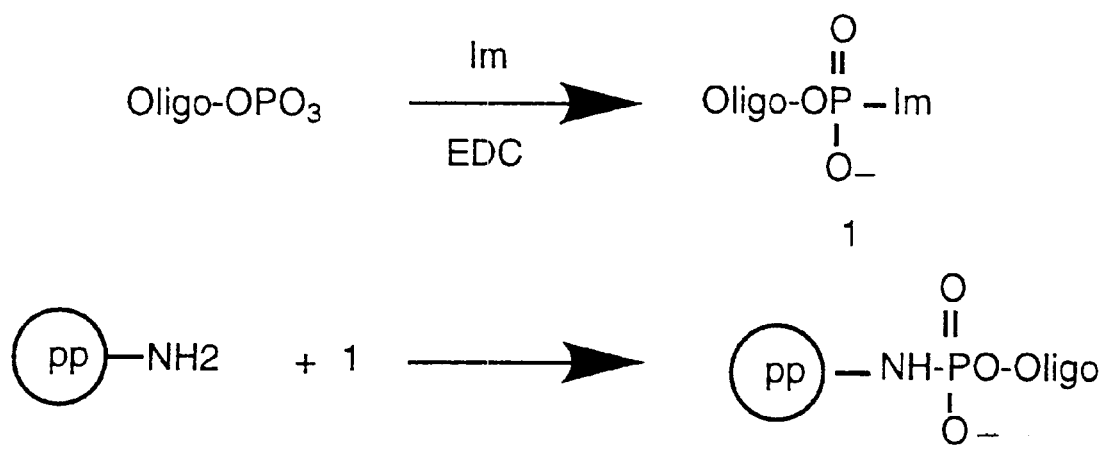
FIG. 1 shows a diagram of an oligonucleotide activation step followed by attachment of the oligonucleotide to an aminated polypropylene support.
Figure 1:

The present method for covalent attachment of oligonucleotides requires a solid-state support that is amenable to surface activation, yet sufficiently chemically inert that unoccupied regions of the surface are not prone to non-specific binding. Moreover, a preferred support material should be generally stable under extremely harsh conditions, e.g. highly basic or acidic reaction or wash conditions.

These criteria are met by using polypropylene, an organic material that can be surface activated, but otherwise is chemically inert under harsh chemical conditions. Polypropylene can be used in very corrosive environments. For example, polypropylene has good chemical resistance to a variety of mineral acids (e.g., hydrochloric acid), organic acids (e.g., formic acid, acetic acid), bases (e.g., ammonium hydroxide, potassium hydroxide), salts (e.g., sodium chloride), oxidizing agents (e.g., peracetic acid, iodine solutions) and organic solvents (e.g. acetone, ethyl alcohol, acetonitrile, etc.). Additionally, polypropylene is hydrophobic and provides low fluorescence background.

Polypropylene has the following chemical structure:

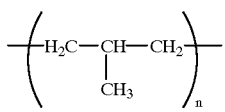

One cannot covalently attach oligonucleotides using unmodified polypropylene as a support material. Thus, in order to attach pre-synthesized oligonucleotides, the polypropylene surface must be modified. For example, amino groups can be introduced onto the surface. An efficient, rapid and economical method for introducing such amino groups onto the surface of a polypropylene medium is by using a plasma discharge in an ammonia or organic amine containing gas.

A "plasma" is most preferably an ionized gas, which gains sufficient ionization energy from an electromagnetic field. It exhibits long range electromagnetic forces and becomes a conductor of electricity. Plasma consists of a mixture of electrons, atoms, positive and negative ions and neutral free radicals. The overall electrical charge of the plasma is neutral. Plasma energy sources include, but are not limited to, direct current, alternating current, radio frequency microwaves, shock waves and lasers. Low temperature plasma treatments include radio frequency plasma discharge ("RFPD") microwave frequency plasma discharge ("MFPD") and corona discharge ("CD"); such treatments all typically affect only the surface of a solid material to a depth of no greater than about 1000→, leaving the remainder of the material unmodified.

Polypropylene can be surface activated via the introduction of amino groups using RFPD, MFPD, or CD in ammonia gas or other suitable amine introducing entities including, but not limited, to $C_1$–$C_{12}$ aliphatic or cyclic amines which may be primary, secondary or tertiary. The hydrocarbon chain can be straight chain, branched, saturated or unsaturated, and one or more amino groups can be attached to the hydrocarbon chain. Methyl amine, alkylamine, ethylenediamine, diaminocyclohexane are examples of such amines. Ammonia is most preferred.

In the presence of a RFPD, MFPD, or CD, the most probable mechanism for the attachment of amino groups to a medium is as follows:

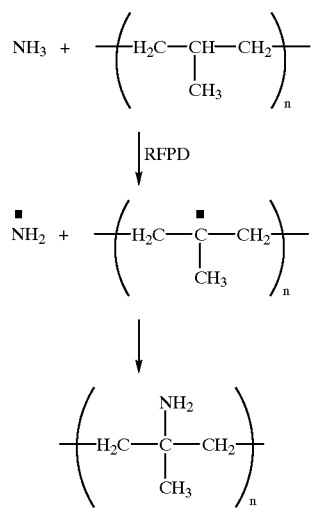

Beneficially, MFPD, RFPD and CD can be efficiently controlled such that only a portion of the polymer medium need be activated. Thus, by activating only a portion of the surface, the remainder continues to be chemically inert. Moreover, only areas which are activated are amenable to the attachment of pre-synthesized oligonucleotides. If such nucleotides are to be used as probes for a genetic trait, problems associated with non-specific binding of nucleic acid macromolecules to the surface are avoided.

Preferably, less than about 50 nmoles per square centimeter ("nmoles/$cm^2$") of the surface of the polypropylene medium is aminated, and more preferably between about 5 to 15 nmoles/$cm^2$. Alternatively, it is preferred that less than about 15%, more preferably less than about 10%, and most preferably less than about 5% of the surface of the polypropylene medium is aminated. The relatively low level of surface amination is intended to minimize non-specific binding to surface sites that may not be occupied by attached oligonucleotides.

Plasma generating devices are commercially available, for example, a particularly preferred plasma generator is available from Plasma Science, Foster City, Calif. (Model No. PS0150E radio-frequency). Such devices are preferred because the conditions for introduction of gases, power, time of plasma discharge, etc. can be readily selected, varied, optimized and controlled. These parameters can be optimized with little experimentation, principally because the physical condition of the polypropylene medium is adversely affected if, for example, the amount of power (typically in watts) is too high, or the length of time of plasma discharge is too great. Such adverse affects are typically manifested by the creation of a "brittle" polymer medium. Accordingly, those skilled in the art are credited with the ability to optimize the conditions for efficient surface amination of the polypropylene medium.

It is preferred that the gas for amination comprises the following components in the following ranges: ammonia (about 99% to about 100%) and oxygen (about 0 to about 1%). Preferably, the wattage of the power supply is between about 10 and about 500 watts, more preferably between about 100 and about 400 watts, and most preferably about 2 minutes.

With respect to the type of plasma discharge, it is preferred that radio frequency waves be utilized; preferably these are within the range of from about 1 MHz to about 20 MHz, and most preferably about 13 MHz. With respect to microwave plasma discharge, it is preferred that the microwaves be in the range of from about 1,000 MHz to about 3,000 MHz, and most preferably about 2,000 MHz. With respect to corona discharge, it is preferred that the treatment power applied is between about 10 to about 250 watts, more preferably at the electrode between about 10,000 and 20,000 volts.

The polypropylene medium can be varied in accordance with the needs of the investigator. As used herein, the term "medium" is intended to mean the physical, structural shape of the polypropylene. Thus, the "medium" can be generally defined as films (i.e., polypropylene having a non-porous surface), membranes (i.e., polypropylene having a porous surface), filaments (e.g. mesh and fabric), beads, microtiter plates, foams, frits, and threads.

Preferably, the polypropylene medium is a film, membrane, or thread. For polypropylene membranes, a thickness of between about 80 to about 100 μm is preferred. In the case of threads, polypropylene having a diameter of about 0.001 inches is preferred.

A particularly preferred embodiment of the invention utilizes biaxially oriented polypropylene film (BOPP). The BOPP can be utilized as a solid-phase activated substrate to support an array or ordered grid of oligonucleotides. The reagents necessary for attaching the pre-synthesized oligonucleotides can be applied either manually or using mechanical reagent dispensing means. Non-porous BOPP films are more durable than microporous membranes and offer a lower fluorescent background. As a consequence, BOPP film is particularly preferred as a support when using mechanical reagent dispensing means and for applications involving fluorescence detection means.

Suitable BOPP films are commercially available, including those available from Catalina Plastics, Calabasas, Calif, or Mobil Chemical Company, Films Division, Pittsford, N.Y., under the trade designations Bicor B and Bicor 100LBW. These films may generally be characterized as high clarity, translucent films of a nominal thickness of about 0.65 to about 2 mils. Those skilled in the art would readily be able to identify other films suitable for use in accordance with the present invention.

The oligonucleotides of the present invention are generally synthesized from nucleotide monomers, consisting of a phosphate group, a 5-carbon sugar, and a nitrogen-containing base. Nucleotide monomers include units having A, G, C, T and U as their bases, as well as analogs and modified forms of the bases. The five carbon sugar can be ribose or 2'-deoxyribose, as well as analogs and modified forms of the sugars. Similarly, the phosphate groups of the oligonucleotides can be replaced by modified forms, such as phosphonate, phosphorothioate, phosponothiate, phosporamidite analogs. Moreover, the phosphate linkages of oligonucleotides can be replaced by a non-phosphorous linkage, such as the neutral peptide-like backbone of peptide nucleic acids (PNA).

Oligonucleotides for attachment to the polypropylene support can be synthesized by solid state methods known in the art, such as the phosphotriester (Beaucage, S. L., et al. Deoxynucleoside phosphoramidites—A new class of key intermediates for deoxypolynucleotide synthesis. *Tetrahedron Lett.* 22:1859–1862 (1981)), H-phosphonate or phosphite triester methods. Instruments for automated solid phase synthesis of oligonucleotides are commercially available, e.g. Oligo 1000 DNA Synthesizer (Beckman Instruments, Fullerton, Calif.). Typically, synthesis of oligonucleotides is performed using the phosphoramidite approach. The 3' hydroxyl group of a first nucleoside is attached to a solid support and the oligonucleotide is synthesized in a 3' to 5' direction. Coupling of subsequent nucleosides to the 5'-hydroxyl of an immobilized oligonucleotide occurs by nucleophilic attack on the phosphoramidite function of a soluble 5'-protected building block. Chain elongation ensues by alternating 5'-deprotection reactions and coupling reactions.

The attachment method of the present invention requires the presence of a terminal phosphate on the pre-synthesized oligonucleotide. This can be conveniently accomplished by directly phosphorylating the 5'-terminus during automated synthesis. For example, a modified cyanoethyl phosphoramidite, e.g. 5'-Phosphate-ON (CLONTECH Laboratories, Palo Alto, Calif.), may be used for the final coupling step of an automated or manual synthesis protocol.

Alternatively, a 3' terminal phosphate may be introduced by using a 3' phosphate CPG or similar solid support as starting material for oligonucleotide synthesis. The oligonucleotide phosphate can then undergo conventional cleavage, deprotection, and purification steps. Alternatively, oligonucleotides may be phosphorylated enzymatically, following cleavage from the solid state support, deprotection, and purification.

The pre-synthesized oligonucleotides that are attached to the polypropylene can have sequences that are perfect complements, imperfect complements, or substantial mismatches to their corresponding target DNAs. Although there is no theoretical upper limit to the length of an oligonucleotide sequence, a minimum length for effective hybridizations is at least about eight nucleotides. In practice, the immobilized oligonucleotides are preferably about ten to about 100 or more nucleotides long, with lengths in the range of 10 up to 35 nucleotide being most preferred.

As shown in FIG. 1, the coupling reaction begins with an activation step, wherein an oligonucleotide having a terminal phosphate is activated to a chemically reactive state. The activation step is accomplished by combining the oligonucleotide with an imidazole, such as N-methylimidazole (NMe-Im) or 4,5-dicyanoimidazole (DCI), and a carbodiimide to form a phosphorimidazolide. The amount of oligonucleotide present in the mixture can range from 1 $\mu$M to about 230 $\mu$M, most preferably about 10 $\mu$M. The imidazole is preferably N-methylimidazole (NMe-Im) or 4,5-dicyanoimidazole (DCI), in amounts ranging from 3 mM to about 100 mM, most preferably about 17 mM. The carbodiimide is preferably a water soluble carbodiimide, most preferably 1-ethyl-3-(3-dimethylaminopropyl)-carbodiimide (EDC), in amounts ranging from 5 mM to about 160 mM, most preferably about 20 mM.

Optionally, a viscous substance, such as glycerol, may be added to the activation mixture to facilitate droplet formation. The formation of discrete droplets may prevent cross-contamination of diverse mixtures during the creation of oligonucleotide arrays on polypropylene films. The amount of glycerol present in the mixture can range from 1% to about 10%, and is typically about 4%.

The activated oligonucleotide mixture is brought into contact with the aminated solid support, typically by using a pipette or an automated dispensing device. A series of droplets comprising different amounts of oligonucleotide or different oligonucleotide sequences may be used to construct an array. The activated oligonucleotide is deposited on the aminated polypropylene for a period of time sufficient to immobilize the oligonucleotide on the solid support. Covalent attachment of the oligonucleotide to aminated polypropylene, by the formation of a phosphoramidate bond, can generally be accomplished at room temperature within 5 min to about 20 hr, depending on the effective concentrations and physical states of the reactants. Preferably, the activated oligonucleotide remains in contact with the aminated polypropylene for about 15 to 60 min.

The activation mixture is then washed from the polypropylene, thereby removing any unattached oligonucleotide from the solid support. The immobilized oligonucleotides will remain attached after repeated washing steps with, e.g. 0.4 M NaOH/10 mM EDTA/0.01% SDS, 2×SSC, and $H_2O$.

The immobilized oligonucleotides can be used for nucleic acid hybridization assays to detect target nucleic acids. Preferred hybridization assays are reverse dot blots, wherein the presence or absence of a target nucleic acid among sample constituents is determined by the application of sample material to oligonucleotides immobilized on a solid support. To be consistent with the reverse dot blot definition, "probe" here refers to oligonucleotides attached to the polypropylene support, while a "target" molecule refers to nucleic acids in solution that may become bound to the surface through the mechanisms of hybridization or non-specific adsorption. Targets can include, but are not limited to, nucleic acids derived from sources implicated in the propagation of infectious disease, e.g. viral or bacterial sources, sequences indicative of genetic abnormalities, and other biologically important nucleic acids.

The target nucleic acids can be any length, but typically are from 10 up to about 2,000 nucleotides in length, and are preferably in the range of about 200 up to about 600 nucleotides in length. Preferred target nucleic acids are obtained by RNA or DNA extraction or by extraction coupled with one or more amplification methods, such as polymerase chain reaction ("PCR").

Various labels can be introduced on the target nucleic acids used in hybridization assays. Alternatively, a labeled detection oligonucleotide, which is complementary to the target, but not the probe, may be utilized in a "sandwich" assay. Such labels act as reporter groups for detecting duplex formation between the target sequence and the probe oligonucleotide. Detectability may be provided by such characteristics as color change, luminescence, fluorescence, or radioactivity.

The labeling procedure may occur prior to analysis (direct labeling) or after hybridization (indirect labeling). An example of indirect labeling would be the biotinylation of a target nucleic acid or detection oligonucleotide. Any biotin moieties retained after hybridization with probe oligonucleotides can bind to an avidin-enzyme conjugate, which then acts on a chromogenic substrate. Labels are preferably fluorescent compounds, such as fluorescein and its derivatives, rhodamine and its derivatives, dansyl, etc. Alternatively, labels can be luminescent compounds, such as luciferin, luminol, and oxetanediones. The above list is not complete, and the label selected may depend on the sensitivity required, the ease of conjugation with target molecules or detection oligonucleotides, and the availability of suitable instrumentation.

Hybridization of the target nucleic acids to the probe oligonucleotides is conducted under conditions that allow stable hybrids to form between complementary regions on the target nucleotide and regions on the probe oligonucleotides. The selection of such conditions is within the level of skill in the art and include those in which a low, substantially zero, percentage of mismatched hybrids form. The precise conditions depend, however, on the desired selectivity and sensitivity of the assay. Such conditions include, but are not limited to, the hybridization temperature, the ionic strength and viscosity of the buffer, and the respective concentrations of the target nucleic acids and probe oligonucleotides.

For example, in certain embodiments the target nucleic acids are hybridized to the probe oligonucleotides at temperatures in the range of about 20°–55° C., for a period in the range of about 0.1 up to about 6 hours, in a suitable hybridization buffer. Preferred hybridization temperatures fall in the range of about 22°–26° C. Preferred hybridization times fall in the range of about 0.5 up to 2 hour and more preferred hybridization times fall in the range of about 1.0 up to about 1.5 hours.

Suitable hybridization buffers for use in the practice of the present invention generally contain a high concentration of salt. An exemplary high salt buffer is 10×SSC, which contains 1.5 M sodium chloride, and 0.15 M sodium citrate, adjusted at a pH of about 7. A typical hybridization buffer contains in the range of about 2–6×SSC and about 0.01% to about 0.5% SDS. An exemplary hybridization buffer is one which contains 6×SSC and 0.01% SDS at pH 7.4.

Once the probe/target hybrid is formed, the resulting complex is washed under conditions suitable to remove substantially all non-specifically bound target nucleic acids and extraneous nucleic acid sequences. Preferably the washing is carried out at a temperature in the range of about 20°–50° C. with a buffer containing about 0.1–2×SSC and 0–0.1% SDS. The most preferred wash conditions presently include a temperature of 22° C. with a buffer containing 2×SSC/0.01% SDS.

EXAMPLES

The following examples, which are neither intended nor to be construed as limiting, are directed to a particularly preferred embodiment of the invention—the amination of polypropylene, followed by the direct attachment of oligonucleotides, for use in the detection of complementary nucleic acid sequences by hybridization techniques.

Materials

Polypropylene film (0.001 in. nominal thickness) was obtained from Catalina Plastics (Calabasas, Calif.), and was aminated using radiofrequency plasma discharge in the presence of anhydrous ammonia gas as delineated above.

Synthesis of oligonucleotide probes and targets was performed on an Oligo 1000 DNA Synthesizer (Beckman Instruments, Fullerton, Calif.) using phosphoramidite-based chemistry protocols. Binary-Pak phosphoramidite and other synthesis reagents were obtained from Beckman Instruments. Probe oligonucleotides having a 5'-phosphate were synthesized by using the 5'-Phosphate-ON reagent (CLONTECH Laboratories, Inc., Palo Alto, Calif.) in the last coupling step of the automated synthesis. Similarly, biotinylated target nucleotides were synthesized using the Biotin-ON Phosphoramidite reagent (CLONTECH Laboratories, Inc., Palo Alto, Calif.) in the last step of the automated synthesis. The purity of the synthetic oligonucleotides was verified using high pressure liquid chromatography (HPLC) or capillary gel electrophoresis (CGE).

Stock solutions of 13 mM 1-methylimidazole (NMe-Im) were prepared fresh daily by dissolving 10.66 mg NMe-Im (Aldrich Chemicals) in 10 ml of HPLC grade $H_2O$. Similarly, stock solutions of 13 mM 4,5-dicyanoimidazole (Aldrich Chemical) and 40 mM EDC (Pierce Chemical) were prepared on the day of experiment by dissolving 15.34 mg of DCI in 10 ml of HPLC grade $H_2O$, and 76.78 mg of EDC in 10 ml of HPLC grade $H_2O$ respectively.

Example 1

Optimum Reaction Times for Attachment of Pre-synthesized H-ras Oligo to Aminopolypropylene The following experiments were conducted to determine suitable conditions for the covalent attachment of a 5'-phospate-oligonucleotide probe for H-ras to aminated polypropylene. The probe and target oligonucleotides used in the following examples have the following nucleotide sequences:

1) H-ras probe (sense)
   A-982:5'-$PO_4$-CCGGCGGTGT-3' (SEQ ID NO:1)

2) H-ras target (antisense)
   A-918:5'-Biotin-ACACCGCCGG-3' (SEQ ID NO:2)
   Two microliters of a 2.64 mM solution of 5'phophorylated oligo A-982 (SEQ ID NO.:1) was combined with 15 μl of 13 mM N-methylimidazole (NMe-Im),5 μl of 40 mM EDC, and about 1 μl of glycerol to give final concentrations of 230 μM oligo, 8.5 mM NMe-Im, 8.7 mM EDC, and about 4% glycerol. Five 1 μspots were pipetted onto four amino polypropylene strips 1 cm wide and 6.6 cm long. Coupling reactions were allowed to proceed on the strips for 5, 15, 30, and 60 min. After attachment the strips were washed twice for 5 min in 10 ml of 2×SSC/0.01% SDS buffer.

The strips were then used in a hybridization reaction to detect the covalently attached probe oligonucleotides. For each strip, 10 μl of 5'biotinylated A-918 (SEQ ID NO: 2), which has a complementary sequence to A-982 (SEQ ID NO.:1), was heated at 92°–95° C. for 10 min, placed on ice for 5 min, and then combined with 90 μl of 6×SSC, 0.01% SDS, pH 7.4 buffer. The final concentration of the biotinylated target DNA was about 10 nM. The entire 100 μM of hybridization solution was pipetted onto a glass microscope slide and each polypropylene strip was placed, DNA side down, on top of the solution. Hybridization was conducted by transferring the glass slide to a petri dish and placing the dish in a shaking water bath for 1 h at 25° C. Each strip was then rinsed 3 times in 20 ml of 2×SSC/0.01% SDS at 22° C.

To detect biotinylated oligo targets, 10 μl of streptavidin-alkaline phosphatase (Tropix, Bedford, Mass.) was diluted with 990 μl of 2×SSC/0.01% SDS buffer and 100 μl of the solution was pipetted onto each of the glass microscope slides. The hybridized strips were placed, with the biotinylated tag DNA side down, onto the 100 μl of solution. The slides were placed in a petri dish and incubated for 1 h at 25° C. in a shaking water bath. Each strip was then rinsed 3 times in 20 ml of 2×SSC/0.01 % SDS. The enzyme substrate, ELF, was prepared by mixing components A and B (1:20) (Molecular Probes, Eugene, OR) and 100 μl per strip was used as described above. After a 30 min incubation the strips were dipped once in 2×SSC/0.01 % SDS and signals were detected using a 254 nm transilluminator and a CCD camera (Photometrics Model CH250), having a 530 nm filter.

Figure 2:
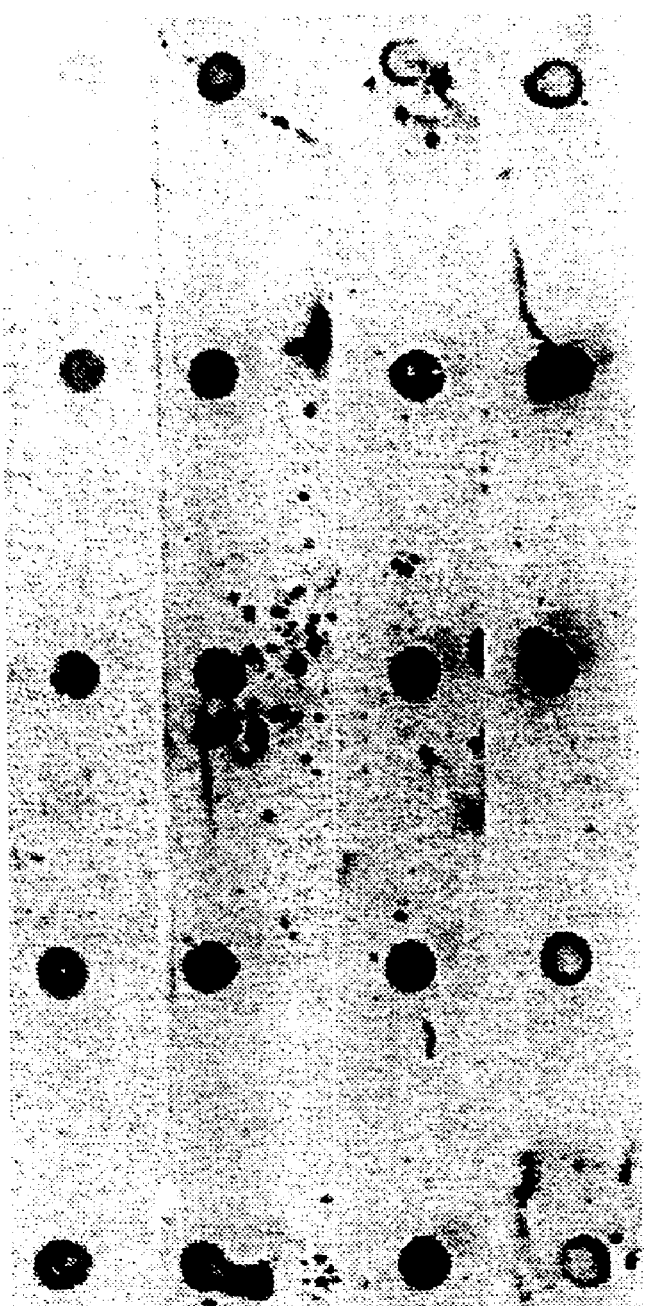
FIG. 2 shows attachment of an H-ras probe oligonucleotide having a 5' terminal phosphate, which was activated and deposited on an aminated polypropylene film for 5, 15, 30, and 60 min, followed by hybridization with a fluorescent-labeled target oligonucleotide.

FIG. 2 shows the signals detected after hybridization and enzyme-labeled fluorescence. The fluorescent spots indicate that detectible amounts of probe oligos were covalently attached to the polypropylene within 5 min. Moreover, the reaction appears to have reached completion by 15 minutes Example 2
Optimum Oligonucleotide Concentrations for Attachment Reactions The following experiment was conducted to determine how much of the 5'phosphorylated oligonucleotide probe is needed as starting material for attachment reactions. A 230 μM solution of probe A-982 was prepared according to Example 1, and diluted in 9.75 mM NMe-Im, 10 mM EDC to give final probe concentrations of 100 μM, 10 μM, 1 μM, 0.1μM, and 0.01 μM. Five 1 μl dots of each dilution were spotted onto aminopropylene strips and incubated for 1 h at 22° C. The strips were washed three times with 2×SSC/0.01% SDS and subjected to hybridization and enzyme-labeled fluorescence detection as described in Example 1.

Figure 3:
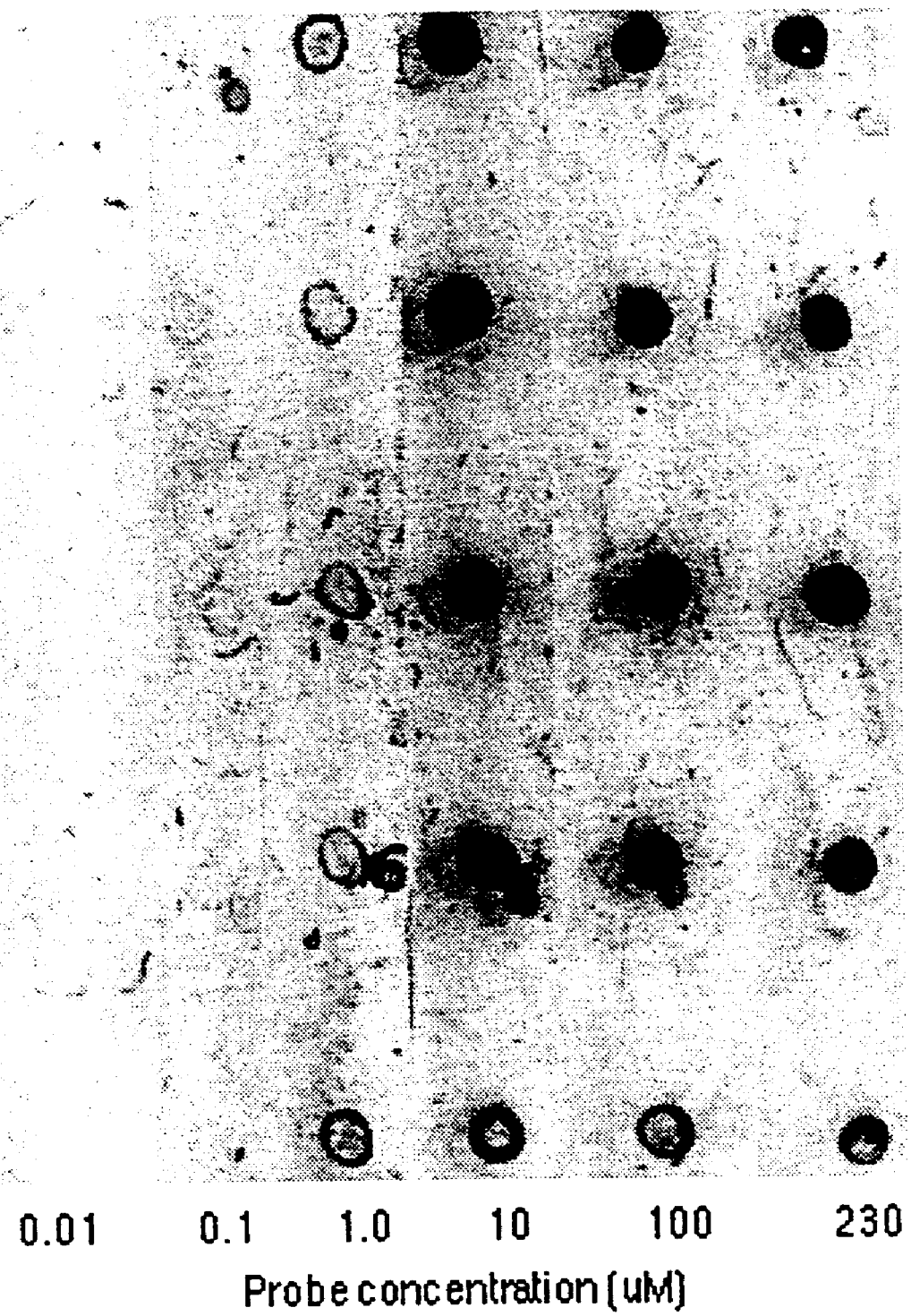
FIG. 3 shows attachment of an H-ras probe oligonucleotide when the concentration of the probe in the reaction mixture was varied, followed by hybridization with a fluorescent-labeled target oligonucleotide.

FIG. 3 shows that detectable amounts of probe became attached to the PPE when at least about 1 μM of oligonucleotide was present in the reaction mixture. Oligonucleotide concentrations of about 10 μM to 230 μM all gave good signals and about 10 μM appears to be optimal.

Figure 4:
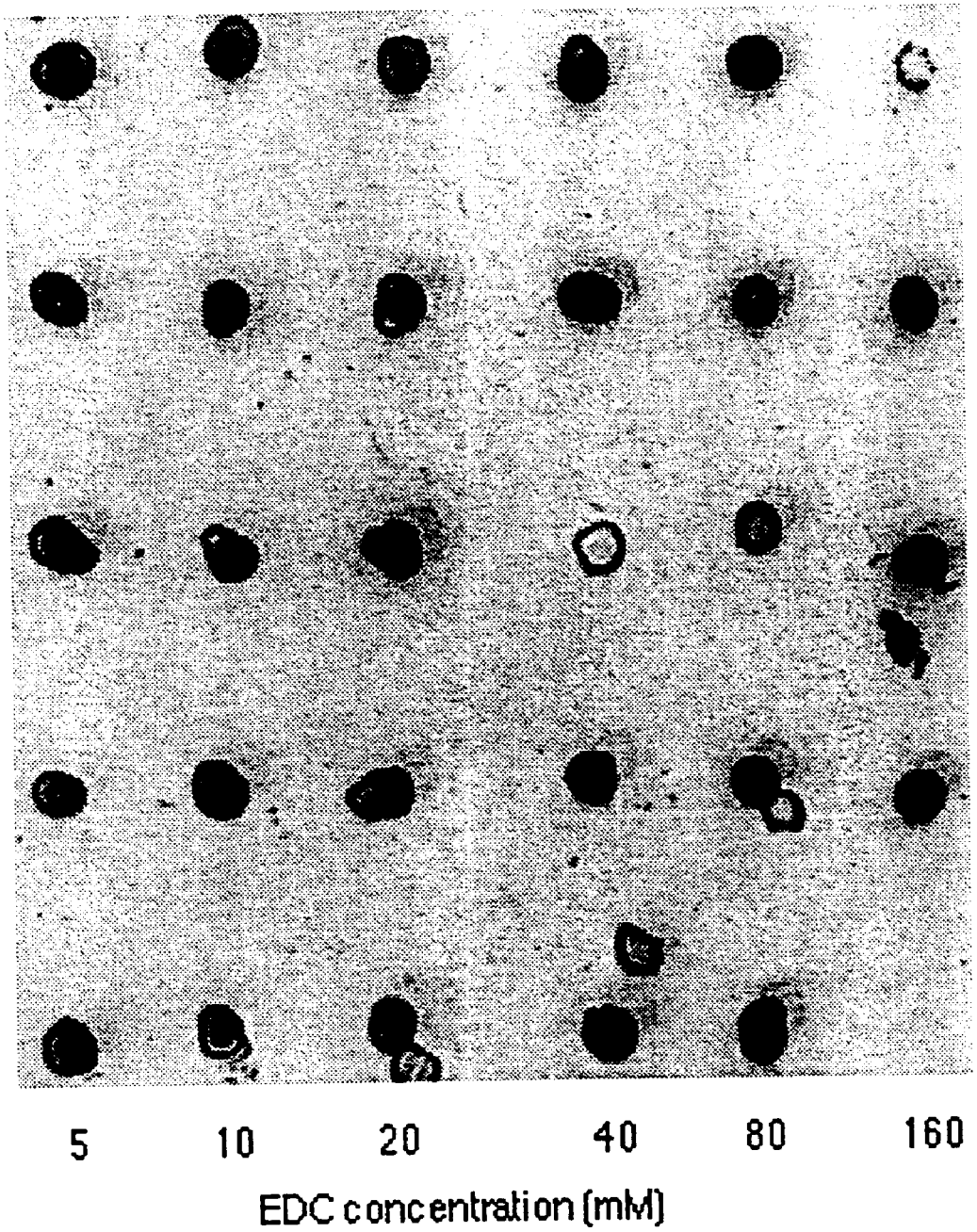
FIG. 4 shows attachment of an H-ras probe oligonucleotide when the concentration of the EDC in the reaction mixture was varied, followed by hybridization with a fluorescent-labeled target oligonucleotide.

Example 3
Optimum Concentrations of EDC for Oligonucleotide Attachment Reactions The following example demonstrates suitable amounts of EDC to be used in the attachment reaction. Six 50 μl reaction mixtures were set up having 10 μM of A-982 probe, 8.77 mM NMe-Im, and 5, 10, 20, 40, 80, or 160 mM EDC. Five 1 μl spots from each mixture was spotted onto strips of aminated polypropylene film, as shown in FIG. 4. After a 1 h incubation at 22° C., the polypropylene strips washed three times with water, three times with 0.4 M NaOH/10 mM EDTA/0.01% SDS (5 min, 10 ml) and three times in 2×SSC/0.01% SDS (5 min, 10 ml). Hybridization and enzyme-labeled fluorescence detection steps were conducted essentially as in Example 1.

As shown in FIG. 3, attachment was detected for all the EDC concentrations tested, i.e. from about 5 mM to about 160 mM, with the strongest signal observed at about 20 mM.

Figure 5:
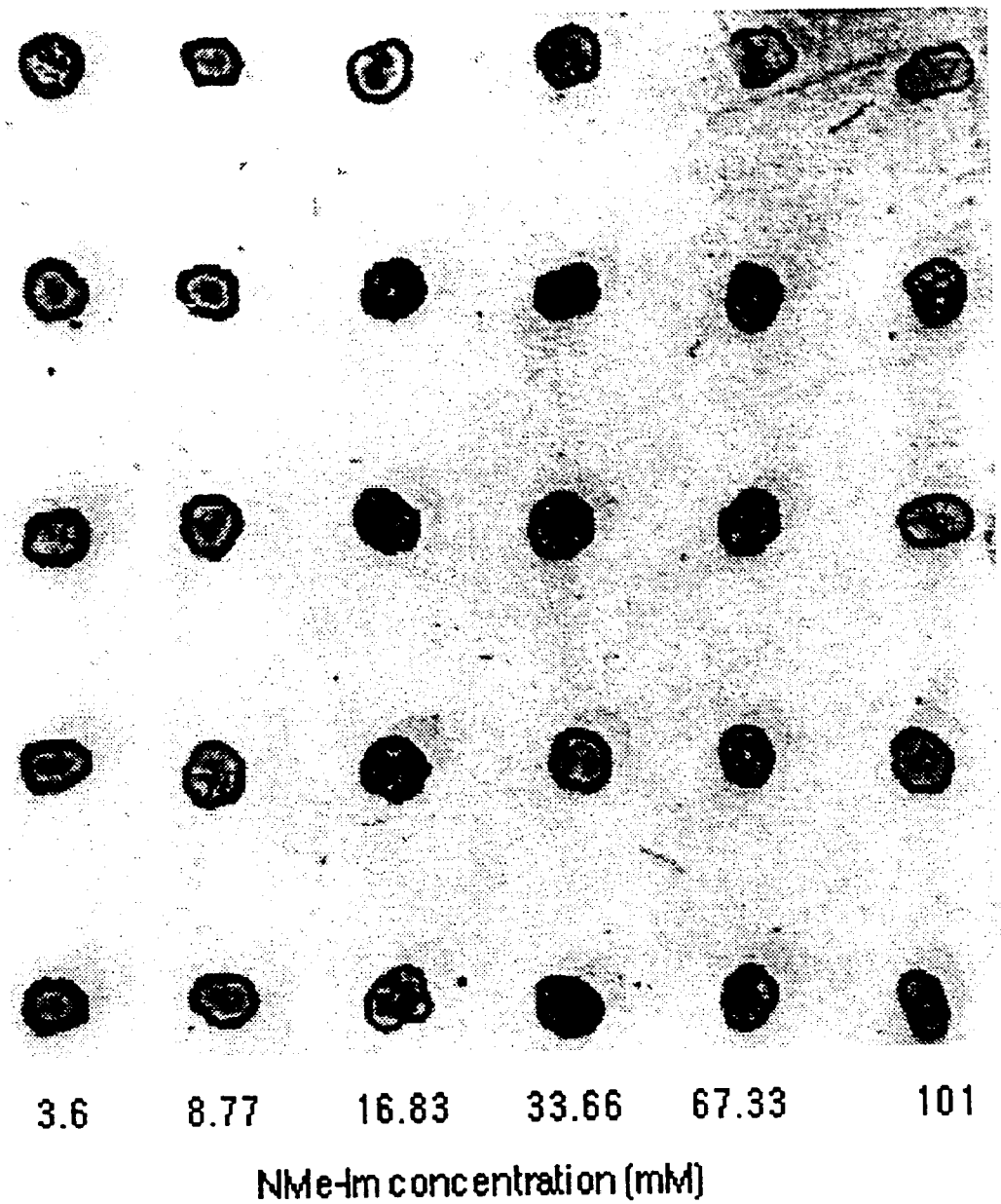
FIG. 5 shows attachment of an H-ras probe oligonucleotide when the concentration of the NMe-Im in the reaction mixture was varied, followed by hybridization with a fluorescent-labeled target oligonucleotide.

Example 4
Optimum Concentrations of NMe-Im for Oligonucleotide Attachment Reactions The following example demonstrates suitable amounts of NMe-Im for conducting the covalent attachment of oligonucleotides to polypropylene. Six 50 μl reaction mixtures were set up having 10 μM of A-982 probe, 20 mM EDC, and 3.36, 8.77,16.83, 33.66, 67.33, or 101 mM NMe-Im. Five 1 μl spots from each mixture was spotted onto strips of aminated polypropylene film, as shown in FIG. 5. After a 1 h incubation at 22° C., the polypropylene strips washed three times with 0.4 M NaOH/10mM EDTA/0.01% SDS (5 min, 10 ml) and three times in 2×SSC/0.01% SDS (5 min, 10 ml). Hybridization and enzyme labeled fluorescence detection steps were conducted essentially as in Example 1.

As shown in FIG. 5, attachment was detected for all the NMe-Im concentrations tested, i.e. from about 3.36 mM to about 101 mM, with the best results observed at about 16.83 mM.

Example 5
Hybridization of Immobilized H-ras Probe with a 63 Base Pair PCR Target The following example shows how a pre-synthesized oligonucleotide probe can be covalently attached to a polypropylene film and used to capture a target, which has been amplified by polymerase chain reaction (PCR). The experiment utilized a 63 base pair amplicon (SEQ ID NOS 3 & 4) of the H-ras wild type proto-oncogene. The specific template DNA (from samples obtained from the Laboratory for Genetic Services, Houston, Tex.) was amplified using PCR protocols essentially as described (Knowles, M. A and Williamson, M., Mutation of H ras is infrequent in bladder cancer: confirmation by single-strand conformation polypmorphism analysis, designed restriction fragment length polymorphisms, and direct sequencing, *Cancer Res.* 53:133–139 (1993)). A Perkin-Elmer Cetus GeneAmp DNA Amplification Reagent Kit with Amplitaq was used according to the manufacturer's instructions. The 63 bp antisense strand (SEQ ID NO: 3) and sense strand (SEQ ID NO: 4) of the H-ras amplicon were as follows:

```
Amplicon Sense Strand
1666 5'-GAC GGA ATA TAA GCT GGT GGT GGT GGG CGC CGG
         CGG TGT GGG CAA GAG TGC GCT GAC CAT CCA-3' 1726

Amplicon Antisense Strand
     5' Biotin-TGG ATG GTC AGC GCA CTC TTG CCC ACA CCG
                CCG GCG CCC ACC ACC ACC AGC TTA TAT TCC GTC-3
```

The bold portion identifies the PCR primers (SEQ ID NOS: 5 & 6); the underlined portions identifies probe sequence B-164 (SEQ ID NO: 7) or its complementary target sequence. The 5' biotinylated reverse primers (SEQ ID NO: 6) for PCR were synthesized on an Oligo 1000 as described above. Forward primers (SEQ ID NO:5) were prepared without a reporter label. The resulting PCR amplicons having 5'biotinylated antisense strands were used without purification. The PCR products were analyzed and confirmed by agarose submarine gel electrophoresis.

A 50 µl reaction mixture was prepared, containing 20 mM EDC, 8.775 mM NMe-Im, 10 µM of oligonucleotide probe B-164 (a 15-mer having a 5' terminal phosphate), and a drop of glycerol. One µl spots were deposited on two plasma aminated polyproplylene films for 60 min at 22° C. After the 60 min coupling reaction, the films were washed in 0.4 M NaOH/10mM EDTA/0.01% SDS.

Before hybridization the polypropylene films, having probe B-164 covalently attached, were washed twice in 2×SSC/0.01%SDS. For a first film, a PCR reaction mixture, JR(B)1 −74, having a DNA concentration of about 75 nM, was used to provide PCR amplicon targets. A 13.3 µl aliquot of the PCR mixture was heated to 95° C. for 10 min and cooled on ice for 5 min. An 86.7 µl amount of 2×SSC/0.01% was added to give a final DNA concentration of about 10 nM in 100 µl of hybridization solution. For a second film, a 10 nM solution of 5'biotinylated oligonucleotide (A-918) in 2×SSC/0.01% SDS was used as a positive control. The polypropylene films were subjected to hybridization and enzyme-labeled fluorescence detection, essentially as described in Example 1.

Figure 6:
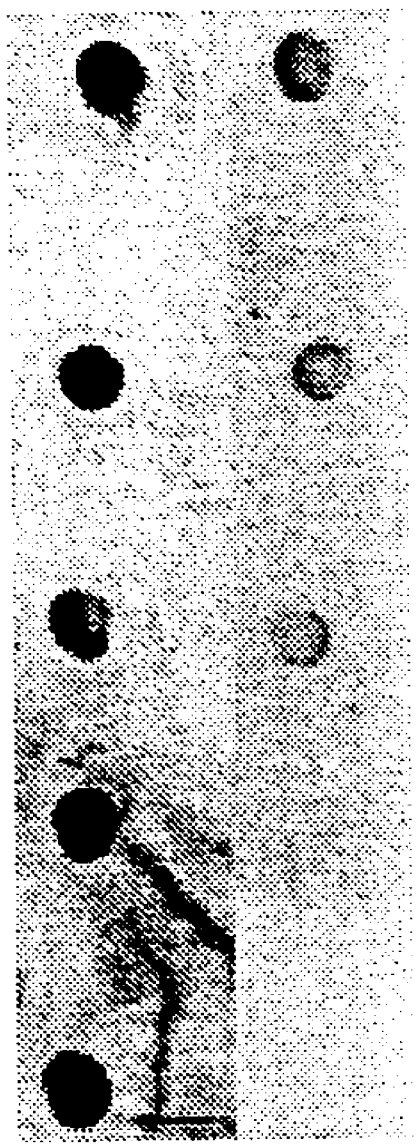
FIG. 6 shows the capture of an H-ras target oligonucleotide (lane 1) and a 63 base pair H-ras amplicon (lane 2) by an H-ras oligonucleotide probe attached to aminated polypropylene.

As shown in FIG. 6, hybridization of the 63 bp PCR products to the immobilized probe gave rise to a detectable signal (lane 2), which was not as intense as the signal for the positive control (lane 1).

Example 6

Attachment of an Oligonucleotide having a 3' Terminal Phosphate

The following example demonstrates that an oligonucleotide having a 3' terminal phosphate can be attached to aminated polypropylene using the methods of the present invention. A synthetic oligonucleotide probe for H-ras, B-166, was synthesized using 3' phosphate-CPG (Glen Research) as solid support during synthesis. The sequence of B-166 15-mer is the same as B-164 (SEQ ID NO: 7), but differs from B-164 in having a 3' terminal phosphate instead of a 5' phosphate.

A 50 µl reaction mixture was prepared, containing 20 mM EDC, 8.775 mM NMe-Im, 10 µM of oligonucleotide probe B-166, and a drop of glycerol. One µl spots were deposited on a plasma aminated polyproplylene film for 60 min at 22° C. After the 60 min coupling reaction, the film was washed in 0.4 M NaOH/10 mM EDTA/0.01% SDS.

Before hybridization the polypropylene film, having probe B-166 covalently attached, was washed twice in 2×SSC/0.01% SDS A 10 nM solution of 5'biotinylated oligonucleotide (A-918) in 2×SSC/0.01% SDS was then used as a target solution for hybridization. The hybridization and subsequent enzyme-labeled fluorescence detection steps were conducted essentially as described in Example 1.

Figure 7:
FIG. 7 shows attachment of an H-ras probe oligonucleotide having a 3' terminal phosphate, which was activated and deposited on an aminated polypropylene film, followed by hybridization with a fluorescent-labeled target oligonucleotide.

As shown in FIG. 7, hybridization of the complementary target oligonucleotide to the immobilized probe gave rise to a detectable signal. However, the signal was not as intense as signals seen in previous examples using probe linked to a 5'-terminal phosphate.

Example 7

Use of 4,5-dicyanoimidazole in Oligonucleotide Attachment:

The following example demonstrates that an oligonucleotide having a terminal phosphate can be attached to aminated polypropylene using 4,5-DCI reagent instead of Nme-Im.

A 50 µl reaction mixture was prepared, containing 20 mM EDC, 8.77 mM 4,5-DCI, 10 µM of the oligonucleotide probe B-166. One µl spots were deposited on a plasma aminated polypropylene film for 60 min. at 22° C. After 60 min. of coupling reaction, the film was washed in 0.4 M NaOH/10 mM ETDA/0.01% SDS. Hybridization and enzyme labeled fluorescence detection steps were conducted essentially as in Example 1.

Figure 8:
FIG. 8 shows attachment of an H-ras probe oligonucleotide when 4,5-dicyanoimidazole was an activating reagent, followed by hybridization with a fluorescent labeled target oligonucleotide.
Figure 8:
Figure 8:
Figure 8:
Figure 8:

As shown in FIG. 8, attachment was performed the 4,5-DCI reagent.

We claim:

1. A method of attaching an oligonucleotide to a solid support, comprising:
   a) aminating the solid support, wherein the support comprises polypropylene;
   b) activating an oligonucleotide having a terminal phosphate by combining the oligonucleotide with an imidazole and a carbodiimide to form a phosphorimidazolide; and
   c) contacting the aminated solid support with the activated oligonucleotide to give an immobilized oligonucleotide attached to the solid support by a phosphoramidate bond.

2. A method according to claim 1, wherein the terminal phosphate is a 5' phosphate.

3. A method according to claim 1, wherein the terminal phosphate is a 3' phosphate.

4. A method according to claim 1, wherein the polypropylene is selected from the group consisting of films, membranes, filaments, beads, microtiter plates, foams, frits, and threads.

5. A method according to claim 1 wherein the oligonucleotide is about 8 to about 100 nucleotides long.

6. A method according to claim 5 wherein the oligonucleotide is about 10 to about 35 nucleotides long.

7. A method according to claim 1 wherein the amount of oligonucleotide present in the activating step ranges from 1 $\mu$M to about 230 $\mu$M.

8. A method according to claim 7 wherein the amount of oligonucleotide is about 10 $\mu$M.

9. A method according to claim 1 wherein the activating step further comprises adding glycerol in an amount ranging from about 1% to about 10%.

10. A method according to claim 1 wherein the contacting step is conducted for a period ranging from about 15 min to about 60 min.

11. A method of capturing a target nucleic acid, comprising:
   a) aminating the solid support, wherein the support comprises polypropylene;
   b) activating a probe oligonucleotide having a terminal phosphate by combining the probe oligonucleotide with an imidazole and a carbodiimide to form a phosphorimidazolide;
   c) contacting the aminated solid support with the activated probe oligonucleotide to give an immobilized probe oligonucleotide attached to the solid support by a phosphoramidate bond;
   d) incubating the immobilized probe oligonucleotide with a hybridization mixture, the hybridization mixture comprising a target nucleic acid; and
   e) detecting the target nucleic acid annealed to the immobilized probe oligonucleotide.

12. A method according to claim 11, wherein the target nucleic acid further comprises a fluorescent label and said detecting step comprises detecting the fluorescent label.

13. A method of attaching an oligonucleotide to a solid support, comprising:
   a) aminating the solid support, wherein the support comprises polypropylene and the polypropylene is aminated by a plasma discharge in an ammonia or organic amine containing gas;
   b) activating an oligonucleotide having a terminal phosphate by combining the oligonucleotide with an imidazole and a carbodiimide to form a phosphorimidazolide; and
   c) contacting the aminated solid support with the activated oligonucleotide to give an immobilized oligonucleotide attached to the solid support by a phosphoramidate bond.

14. A method according to claim 13, wherein the plasma discharge is selected from the group consisting of radio frequency plasma discharge, microwave frequency discharge, and corona discharge.

15. A method according to claim 13, wherein the plasma discharge occurs in an ammonia containing gas.

16. A method according to claim 13, wherein the plasma discharge occurs in an organic amine containing gas, the organic amine being selected from the group consisting of methyl amine, alkylamine, ethylenediamine, and diaminocyclohexane.

17. A method of attaching an oligonucleotide to a solid support, comprising:
   a) aminating the solid support, wherein the support comprises polypropylene;
   b) activating an oligonucleotide having a terminal phosphate by combining the oligonucleotide with an imidazole and a carbodiimide to form a phosphorimidazolide, wherein the imidazole is N-methylimidazole or 4,5-dicyanoimidazole; and
   c) contacting the aminated solid support with the activated oligonucleotide to give an immobilized oligonucleotide attached to the solid support by a phosphoramidate bond.

18. A method according to claim 17, wherein the N-methylimidazole or 4,5-dicyanoimidazole is present in an amount ranging from 3 mM to about 100 mM.

19. A method according to claim 17, wherein the N-methylimidazole or 4,5-dicyanoimidazole is present in an amount of about 17 mM.

20. A method according to claim 17, wherein the carbodiimide is 1-ethyl-3-(3-dimethylaminopropyl)-carbodiimide (EDC).

21. A method according to claim 20 wherein the EDC is present in an amount ranging from 5 mM to about 160 mM.

22. A method according to claim 20 wherein the EDC is present in an amount of about 20 mM.

23. A method of attaching an oligonucleotide to a solid support, comprising:
   a) aminating the solid support, wherein the support comprises polypropylene;
   b) activating an oligonucleotide having a terminal phosphate by combining the oligonucleotide with an imidazole and 1-ethyl-3-(3-dimethylaminopropyl)-carbodiimide (EDC) to form a phosphorimidazolide; and
   c) contacting the aminated solid support with the activated oligonucleotide to give an immobilized oligonucleotide attached to the solid support by a phosphoramidate bond.

24. A method of attaching an oligonucleotide to a solid support, comprising:
   a) aminating the solid support, wherein the support comprises polypropylene and the polypropylene is aminated by a plasma discharge in an ammonia or organic amine containing gas;
   b) activating an oligonucleotide having a terminal phosphate by combining the oligonucleotide with an imidazole, wherein the imidazole is N-methylimidazole or 4,5-dicyanoimidazole, and 1-ethyl-3-(3-dimethylaminopropyl)-carbodiimide (EDC) to form a phosphorimidazolide; and
   c) contacting the aminated solid support with the activated oligonucleotide to give an immobilized oligonucleotide attached to the solid support by a phosphoramidate bond.

* * * * *

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<220> FEATURE:
<223> OTHER INFORMATION: Description of Artificial Sequence: synthetic
      oligonucleotide

<400> SEQUENCE: 1
ccggcggtgt                                                          10

<210> SEQ ID NO 2
<211> LENGTH: 10
<212> TYPE: DNA
<213> ORGANISM: Artificial Sequence
<220> FEATURE:
<220> FEATURE:
<223> OTHER INFORMATION: Description of Artificial Sequence: synthetic
      oligonucleotide

```
<400> SEQUENCE: 2
acaccgccgg                                                           10

<210> SEQ ID NO 3
<211> LENGTH: 63
<212> TYPE: DNA
<213> ORGANISM: Artificial Sequence
<220> FEATURE:
<220> FEATURE:
<223> OTHER INFORMATION: Description of Artificial Sequence: synthetic
      oligonucleotide

<400> SEQUENCE: 3
gacggaatat aagctggtgg tggtgggcgc cggcggtgtg ggcaagagtg cgctgaccat     60
cca                                                                  63

<210> SEQ ID NO 4
<211> LENGTH: 63
<212> TYPE: DNA
<213> ORGANISM: Artificial Sequence
<220> FEATURE:
<220> FEATURE:
<223> OTHER INFORMATION: Description of Artificial Sequence: synthetic
      oligonucleotide

<400> SEQUENCE: 4
tggatggtca gcgcactctt gcccacaccg ccggcgccca ccaccaccag cttatattcc     60
gtc                                                                  63

<210> SEQ ID NO 5
<211> LENGTH: 20
<212> TYPE: DNA
<213> ORGANISM: Artificial Sequence
<220> FEATURE:
<220> FEATURE:
<223> OTHER INFORMATION: Description of Artificial Sequence: synthetic
      oligonucleotide

<400> SEQUENCE: 5
gacggaatat aagctggtgg                                                20

<210> SEQ ID NO 6
<211> LENGTH: 20
<212> TYPE: DNA
<213> ORGANISM: Artificial Sequence
<220> FEATURE:
<220> FEATURE:
<223> OTHER INFORMATION: Description of Artificial Sequence: synthetic
      oligonucleotide

<400> SEQUENCE: 6
tggatggtca gcgcactctt                                                20

<210> SEQ ID NO 7
<211> LENGTH: 15
<212> TYPE: DNA
<213> ORGANISM: Artificial Sequence
<220> FEATURE:
<220> FEATURE:
<223> OTHER INFORMATION: Description of Artificial Sequence: synthetic
      oligonucleotide

<400> SEQUENCE: 7
gccggcggtg tgggc                                                     15
```